United States Patent
Yen et al.

(10) Patent No.: US 8,900,143 B2
(45) Date of Patent: Dec. 2, 2014

(54) INTRAOCULAR PRESSURE DETECTING DEVICE AND DETECTING METHOD THEREOF

(75) Inventors: Meng-Shin Yen, Taipei (TW); William Wang, Taoyuan (TW); Chung-Cheng Chou, Taoyuan County (TW)

(73) Assignee: Crystalvue Medical Corporation, Gueishan, Taoyuan (TW)

( * ) Notice: Subject to any disclaimer, the term of this patent is extended or adjusted under 35 U.S.C. 154(b) by 386 days.

(21) Appl. No.: 13/434,504

(22) Filed: Mar. 29, 2012

(65) Prior Publication Data
US 2012/0253165 A1    Oct. 4, 2012

(30) Foreign Application Priority Data
Mar. 29, 2011    (TW) .............................. 100110702 A (51) Int. Cl.
*A61B 3/16*    (2006.01)
(52) U.S. Cl.
CPC ........................................ *A61B 3/16* (2013.01)
USPC .......................................................... 600/398

(58) Field of Classification Search
CPC ........... A61B 3/16; A61B 3/008; A61B 3/165
USPC .................................................. 600/398–405
See application file for complete search history.

(56) References Cited

U.S. PATENT DOCUMENTS 4,523,597 A * 6/1985 Sawa et al. .................... 600/405

* cited by examiner

*Primary Examiner* — Max Hindenburg
*Assistant Examiner* — Jonathan M Foreman
(74) *Attorney, Agent, or Firm* — Muncy, Geissler, Olds & Lowe, P.C.

(57) ABSTRACT

An intraocular pressure detecting device includes an image capturing unit, a processor, and a pressure detection unit. The image capturing unit, coupled to the image capturing unit, is capable of acquiring an eye image. According to the eye image, the processor can determine an intraocular pressure detection area. After the pressure detection unit detects the intraocular pressure detection area, the intraocular pressure is calculated by the processor of the intraocular pressure detecting device.

14 Claims, 6 Drawing Sheets

INTRAOCULAR PRESSURE DETECTING DEVICE AND DETECTING METHOD THEREOF

BACKGROUND OF THE INVENTION

1. Field of the Invention

The present invention generally relates to an intraocular pressure detecting device. Particularly, the present invention relates to an intraocular pressure detecting device capable of determining an intraocular pressure detection area.

2. Description of the Prior Art

The conventional intraocular pressure detecting device for testing and controlling eye fluid pressure includes a surgical apparatus for penetrating into eyeballs. A fluid pressure convertor is installed on the surgical apparatus, such that when the surgical apparatus penetrates the eye, the fluid pressure convertor is positioned near the opening. Since the opening communicates with the interior of the eye, the fluid pressure convertor is able to react to the change in fluid pressure within the eye and correspondingly generate a signal to reflect such change in fluid pressure. In other words, conventional intraocular pressure measuring devices are devices invasive to the eye and are generally unwelcomed by the general public.

Recent generations of intraocular pressure detecting devices include non-invasive devices that are slowly displacing the conventional invasive intraocular pressure detecting devices. Non-invasive intraocular pressure detecting devices can be classified as contact or non-contact forms. In either forms, an external force is exerted on the cornea in order to extrapolate an intraocular pressure measurement from the relationship between the external force and the deformation of the cornea. However, research has shown that the curvature as well as the thickness of the cornea provides a certain margin of error in the actual intraocular pressure readings. Therefore, it is of major significance to the current industry to research and develop intraocular pressure detecting devices capable of determining appropriate intraocular pressure detection areas.

SUMMARY OF THE INVENTION

It is an object of the present invention to provide an intraocular pressure detecting device and an intraocular pressuring detecting method thereof, capable of determining appropriate intraocular pressure detection areas.

The intraocular pressure detecting device includes an image capturing unit, a processor unit, and a pressure detection unit. The image capturing unit is used for capturing an eye image. The processor unit is electrically coupled to the image capturing unit and determines an intraocular pressure detection area in accordance to the eye image. After determining the intraocular pressure detection area, the pressure detection unit detects the intraocular pressure detection area and correspondingly generates a pressure detection signal, wherein the processor unit determines an intraocular pressure according to the pressure detection signal.

The intraocular pressure detecting method includes the steps of capturing the eye image, analyzing the eye image and determining the intraocular pressure detection area, measuring the intraocular pressure of the intraocular pressure detection area and correspondingly generating the pressure detection signal, analyzing and comparing the pressure detection signal, and determining the intraocular pressure.

DETAILED DESCRIPTION OF THE PREFERRED EMBODIMENT

Figure 1:
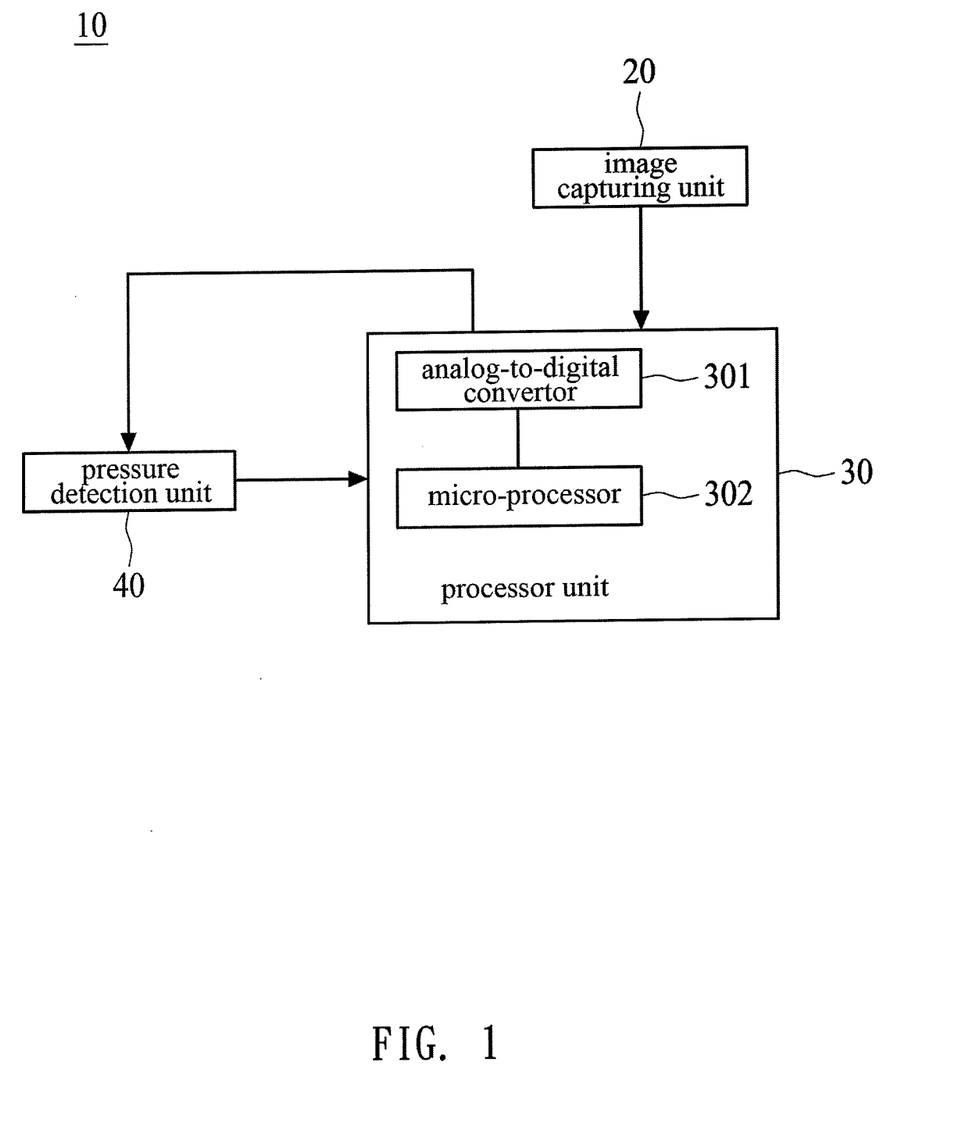
FIG. 1 is a schematic diagram of an embodiment of the intraocular pressure detecting device.
Figure 2:
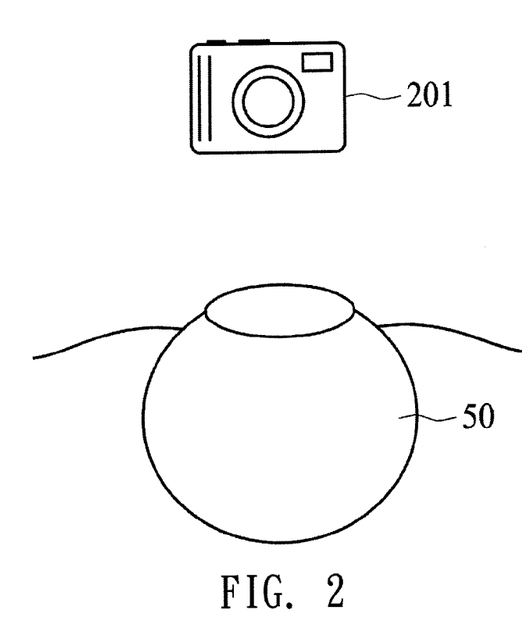
FIG. 2 is an embodiment of the image capturing unit capturing the eye image.
Figure 3:
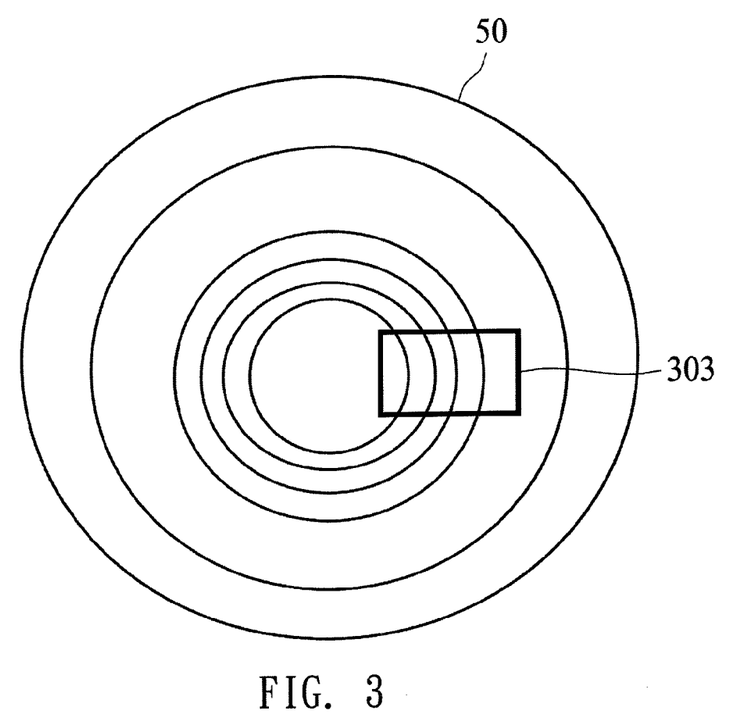
FIG. 3 is an embodiment of the processor unit determining the intraocular pressure detection area.

Referring to FIG. 1, an intraocular pressure detecting device 10 includes an image capturing unit 20, a processor unit 30, and a pressure detection unit 40. As shown in FIGS. 1 and 2, the image capturing unit 20 may be used to capture images of an eye 50. In the present embodiment, the image capturing unit 20 may be a photographic device 201. Specifically, the photographic device 201 may be a CCD (Charge Coupled Device) photographic camera or a CMOS (Complementary Metal Oxide Semiconductor) photographic camera, wherein the photographic device may be focused with wide-angle reflection mirrors in order to capture a panoramic image of the eye 50. Since intraocular pressure may not be determined from surfaces other than the surface of the eye, such as wounds and other areas where intraocular pressure may be difficult to measure, the image of the eye 50 captured by the photographic device 201 may be selected from a cornea image, an eyelid image, an eyebrow image, and an orbit image to provide position for the overall eye and for selecting an intraocular pressure detection area 303 (as shown in FIG. 3).

The image capturing unit 20 may also be a photoelastic stress analyzer, providing stress distribution of the corneal area. Projected light from the photoelastic stress analyzer is composed of two light components: a light component parallel to the force an eye experiences (ex. intraocular pressure) and a light component perpendicular to the same force. Since the speed of light is proportional to the pressure, the projected light (and thus the two components) will travel through the eye at different speeds according to different pressures, resulting in phase shift. If the phase shift is constructive, the two components will be additive and form a bright area. However, if the phase shift causes the two components to be mutually disruptive, a dark area will be formed. In this manner, the lines formed by the bright and dark areas on the eye may be observed and analyzed by the photoelastic stress analyzer to calculate and explain the pressure gradient distribution of cornea, as shown in FIG. 3. In addition, the pressure gradient distribution of cornea facilitates the selection of the intraocular pressure detection area 303 in order to further carry out the intraocular pressure measurement.

As shown in FIGS. 1 and 2, whether the image capturing unit 20 is the photographic device 201 or the photoelastic stress analyzer, when the intraocular pressure detecting device 10 of the present invention determines a need to track a specific area of the eye 50, the field of view of the panoramic image captured by the image capturing unit 20 may be adjusted by the intraocular pressure detecting device 10. When the image capturing unit 20 detects the mentioned specific area of the eye 50, the intraocular pressure detecting device 10 may be utilized to rotate or shift to move the position of the focal point, such as moving the focal point from the eyelid to the cornea or any other positions on the eye 50, such that the function of dynamic tracking of the eye 50 may be achieved. Furthermore, in other embodiments, the image capturing unit 20 may also adjust the resolution of the panoramic image view of the eye 50 by way of the electrical coupling with an optical focusing unit (not shown).

As shown in FIG. 1, the processor unit 30 is electrically coupled to the image capturing unit 20 (e.g. photographic device 201 or intraocular pressure analyzer), wherein the processor unit 30 includes an analog-to-digital convertor 301 and a microprocessor 302. The image of the eye 50 and the eye image signal is transmitted to and processed in the analog-to-digital convertor 301 to generate an eye image electrical signal. The microprocessor 302 analyzes the eye image electrical signal to find preferable detection areas of the pressure gradient distribution in order to determine a suitable intraocular pressure detection area 303, as shown in FIG. 3. Simply, the processor unit 30 determines the intraocular pressure detection area 303 according to the image of the eye 50 and the eye image signal.

Figure 4:
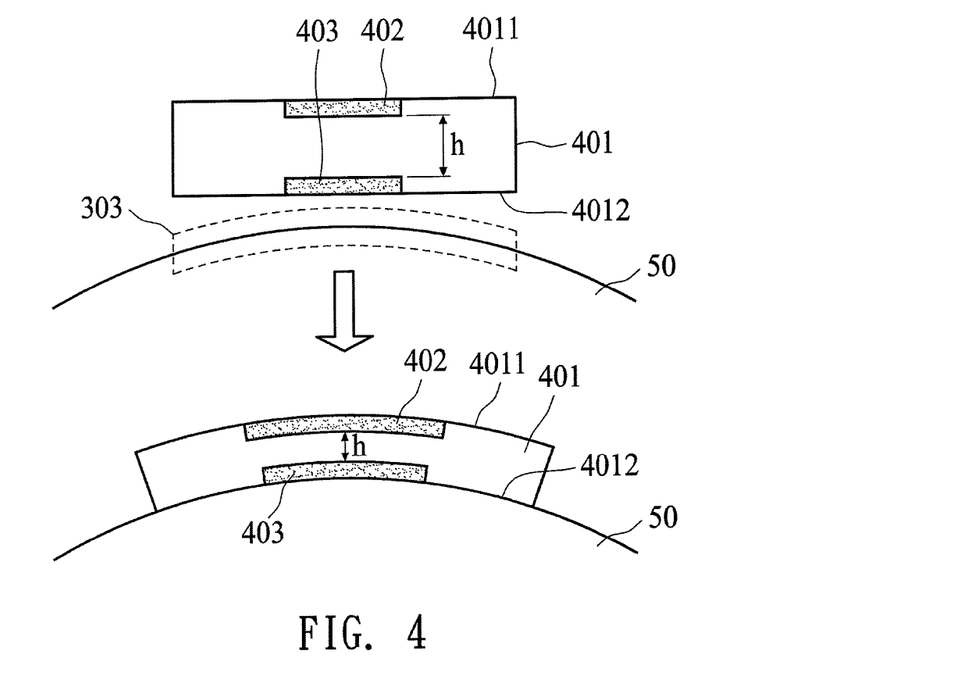
FIG. 4 is an embodiment of the pressure detection unit measuring the intraocular pressure detection area of the eye.

Since the curvature and thickness of the cornea produces a bias in the actual value of the measured intraocular pressure, the determination of the intraocular pressure detection area is, in practice, very important to the measurement of the intraocular pressure. As shown in FIGS. 1, 3, and 4, in order to precisely measure the actual intraocular pressure, a pressure detection unit 40 proceeds with intraocular pressure testing on the intraocular test area 303 after the intraocular test area 303 has been determined.

Figure 5:
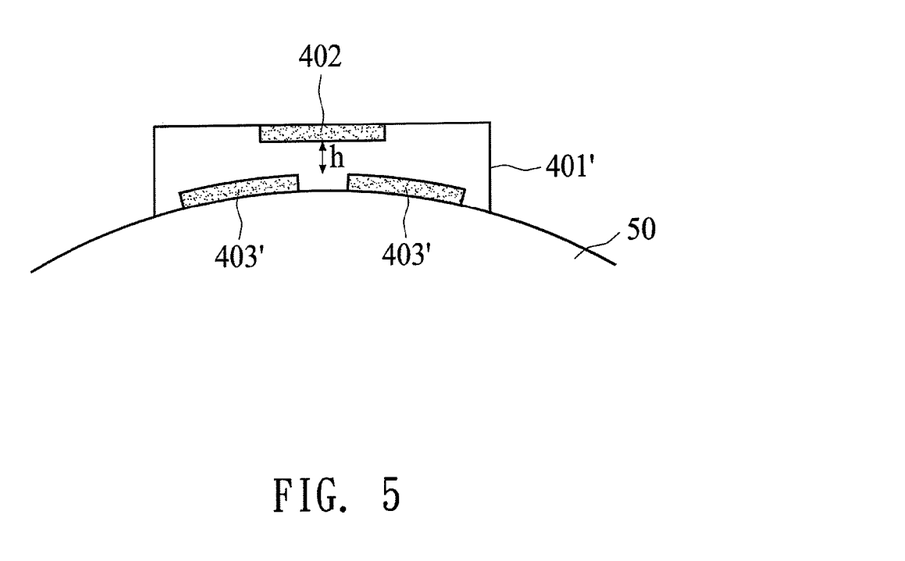
FIG. 5 is another embodiment of the pressure detection unit measuring the intraocular pressure detection area of the eye.

As shown in FIG. 4, the pressure detection unit 40 is an elastic member 401. Elastic member 401 includes a first electrode 402 and a second electrode 403. Since the elastic member 401 is formed from dielectric materials, the first electrode 402 and the second electrode 403 may form a capacitive sensor device. In other words, the pressure detection unit 40, in the present embodiment, conducts intraocular pressure measurements through the capacitive sensor device by direct contact. As shown in FIG. 4, the first electrode 402 and the second electrode 403 of the pressure detection unit 40 are respectively disposed on a top surface 4011 and a bottom surface 4012 of the elastic member 401. As the elastic member 401 comes in contact with the eye 50, the elastic member 401 will deform, which leads to a difference in the space h between the first electrode 402 and the second electrode 403. This difference in the space h may be used to measure dynamic changes in the intraocular pressure. In the present embodiment, the first electrode 402 and the second electrode 403 are arranged symmetrically. However, in other embodiments such as shown in FIG. 5, the first electrode 402 and the second electrode 403' of the elastic member 401' may be arranged asymmetrically. The symmetric or asymmetric arrangement mentioned above refers to whether or not the first electrode 402 on the top surface 4011 of the elastic member 401 or 401' are symmetrically arranged in the vertical direction with the second electrode 403 or 403' on the bottom surface. Specifically, the vertical directions of the first electrode 402 and the second electrode 403 or 403' are parallel with the spacing h between the first electrode 402 and the second electrode 403.

Figure 6:
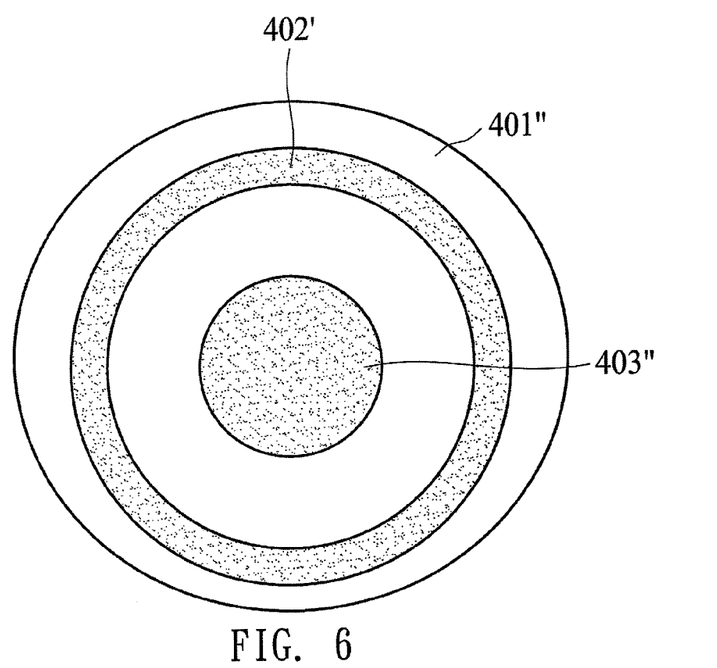
FIG. 6 is a top view of another embodiment of the elastic member of the pressure detection unit.
Figure 7:
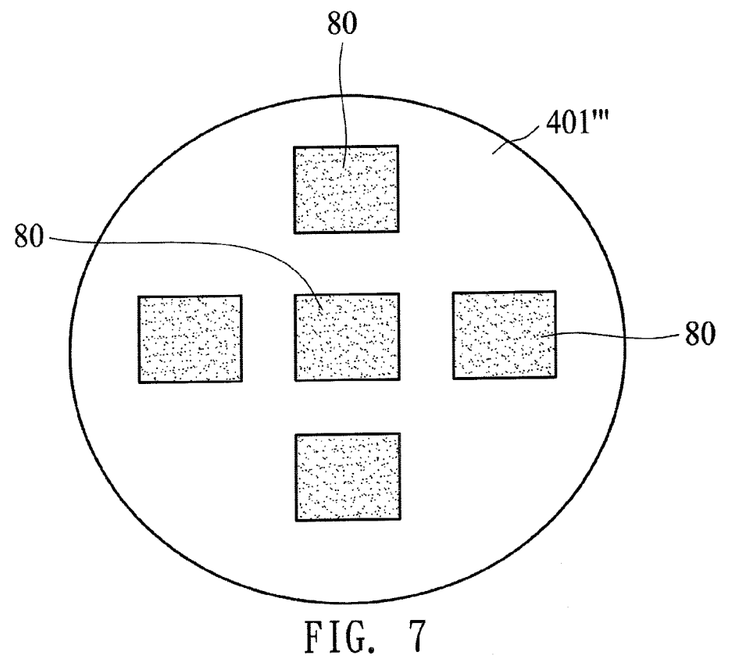
FIG. 7 is a top view of yet another embodiment of the elastic member.

The embodiment shown in FIG. 6 illustrates a top view of an elastic member 401". The first electrode 402' and the second electrode 403" may be arranged on the elastic member 401" as rings on the same plane. As seen in the top view diagram of an embodiment of an elastic member 401''', in order to strengthen the effects of the capacitive change, a plurality of electrodes 80 may be arranged as rectangles that are adjacent to each other such that the capacitive sensing area between the electrodes 80 is in practice much bigger. In addition to being able to measure the dynamic changes to the intraocular pressures, the elastic members 401" and 401''' with the large surface areas of FIGS. 6 and 7 may also utilize the capacitive sensing between the wide area ranged electrodes to measure the curvature of the intraocular pressure detection area 303. Therefore, the elastic members 401" and 401''', in addition to being able to measure the dynamic changes to intraocular pressures, they can also measure the curvature of the cornea such that the bias in the measurement of the intraocular pressure due to the curvature of the cornea or cornea thickness within the intraocular pressure detection area 303 may be reduced.

Figures 8, 9:
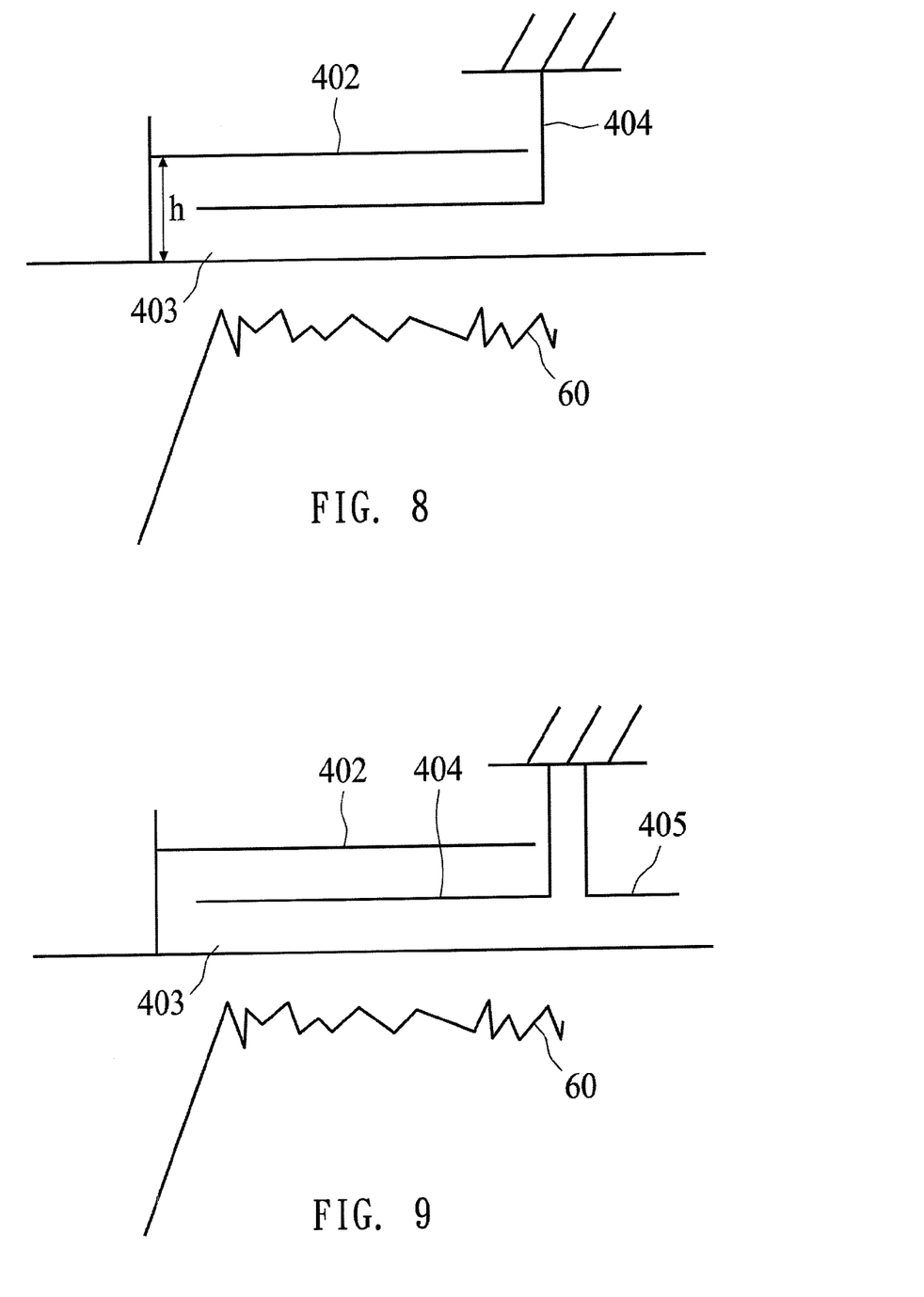
FIG. 8 is a diagram of an embodiment of the third electrode raising the signal-to-noise ratio.
FIG. 9 is a diagram of an embodiment of the vibrations directly detected in the intraocular pressure detection area by a reference electrode of the elastic member.

Usually, the inner pressures within the eye, or more commonly known as the intraocular pressure, will cause high frequency vibrations of the cornea. These vibrations will cause the space h between the electrodes to change and result in the transmission of signal. As shown in FIG. 8, dynamic changes (such as high frequency vibrations) to the intraocular pressure may be deduced from the changes in the space h between the first electrode 402 and the second electrode 403 due to the deformation of the elastic member 401. Specifically, the changes to the space h between the first electrode 402 and the second electrode 403 will generate a pressure detection signal 60, wherein the processor unit 30 will then determine an intraocular pressure according to the pressure detection signal 60. As shown in FIGS. 1 and 8, the pressure detection signal 60 measured by the pressure detection unit 40 will be transmitted back to the processor unit 30. Once the analog-to-digital converter of the processor unit 30 processes the pressure detection signal 60, the signal is then transmitted to the micro-processor 302. The micro-processor 302 compares the processed pressure detection signal 60 to the corresponding intraocular pressure and determines the intraocular pressure of the eye 50.

As shown in FIG. 8, in order to further decrease signal noise, the elastic member 401 further includes a third electrode 404, wherein the third electrode 404 is disposed between the first electrode 402 and the second electrode 403. Since the third electrode 404 is disposed between the first electrode 402 and the second electrode 403, when the space h between the first electrode 402 and the second electrode 403 changes, the third electrode 404 is able to provide signals pertaining to the space between the first electrode 402 and the third electrode 404, as well as the space between the second electrode 403 and the third electrode 404. In this manner, signal noise may be decreased while the accuracy of the pressure detection signal between the first electrode 402 and the second electrode 403 is increased, raising the signal-to-noise ratio as a result. The signal-to-noise ratio referred to herein is defined by the ratio of the signal divided by the signal noise.

As shown in FIG. 9, the elastic member 401 further includes a reference electrode 405, wherein the reference electrode 405 can directly detect vibrations of the intraocular pressure detection area 303. The vibrations may be compared to a default database, wherein the vibrations may be classified as low frequency vibrations from eye movements or as high frequency vibrations from intraocular pressures such that, in practice, misjudgment cases may be reduced.

The above mentioned embodiments deal with the elastic member 401 proceeding with the detection through direct contact methods. However, the image capturing unit 20 may also capture the eye image to produce the eye image signal through non-contact methods. The eye image (and subsequently the eye image signal) includes a cornea image, an eyelid image, an eyebrow image, and an orbit image. The eye image 50 and the eye image signal are transmitted to the analog-to-digital converter 301 of the processor unit 30 to generate the eye image electrical signal. The micro-processor 302 compares and analyzes the eye image electrical signal to find preferable detection areas of the pressure gradient distribution in order to determine a suitable pressure detection area 303. The image capturing unit 20 can detect tomography graphs of the pressure detection area 303 and then utilize changes in the time domain pattern matching analysis to obtain the pressure detection signal resulting from the intraocular pressure. Specifically, the image capturing unit 20 may simultaneously provide functions of the pressure detection unit 40. The image capturing unit 20 is not limited to the embodiment shown in FIG. 2, as it can also be other optical image capturing units that can receive optical signals. In practice, the image capturing unit 20 utilizes principles of optical interference to capture the eye image signal. These eye image signals include the mentioned cornea thickness data, corneal section image data, and corneal curvature data. After the mentioned data are transmitted to the micro-processor 302, in addition to being able to determine the intraocular pressure detection area, the micro-processor 302 may also correct the interpretation of the intraocular pressure. During the intraocular pressure detection procedures, the image capturing unit 20 can provide corneal section images of differing time domains. Through processing by the micro-processor 302, the high frequency vibrations (i.e. pressure detection signal 60) generated by the cornea when the cornea is under intraocular pressure can be obtained. The micro-processor 302 then compares the pressure detection signal 60 to the corresponding intraocular pressure and determines the intraocular pressure of the eye 50. This principle is the same as utilizing the changes in capacitance generated by the high frequency vibrations of the cornea.

Figure 10:
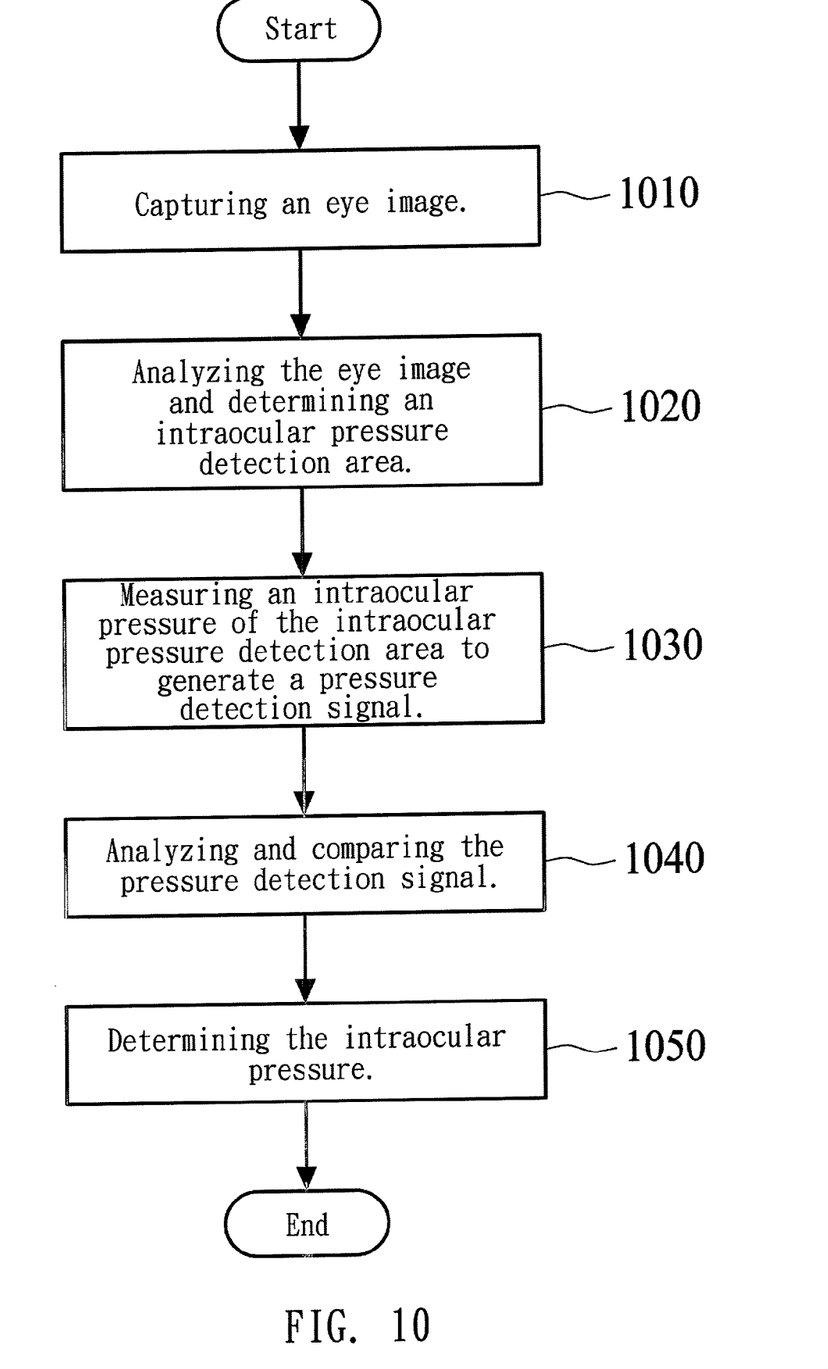
FIG. 10 is a flow chart diagram of an embodiment of the intraocular pressure detecting method.

As shown in FIG. 10 of an intraocular pressure detecting method, the method includes the following steps. Step 1010 involves capturing an eye image. Step 1020 involves analyzing the eye image and determining an intraocular pressure detection area. Step 1030 involves measuring an intraocular pressure of the intraocular pressure detection area to generate a pressure detection signal. Step 1040 involves analyzing and comparing the pressure detection signal. Step 1050 involves determining the intraocular pressure.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. An intraocular pressure detecting device, comprising:
an image capturing unit for capturing an eye image;
a processor unit electrically coupled to the image capturing unit for determining an intraocular pressure detection area according to the eye image, wherein the eye image comprises corneal thickness data, corneal section data, and corneal curvature data;
a pressure detection unit for detecting the intraocular pressure detection area and generating a pressure detection signal, wherein the processor unit determines an intraocular pressure according to the pressure detection signal.

2. The intraocular pressure detecting device of claim 1, wherein the image capturing unit comprises a photographic device, the photographic device capturing the eye image.

3. The intraocular pressure detecting device of claim 2, wherein the eye image is selected from a cornea image, an eyelid image, an eyebrow image, and an orbit image.

4. The intraocular pressure detecting device of claim 1, wherein the processor unit comprises an analog-to-digital converter and a microprocessor, the analog-to-digital converter processes the eye image into an eye image signal, the micro-processor analyzes the eye image signal and determines the intraocular pressure detection area.

5. The intraocular pressure detecting device of claim 1, wherein the pressure detection unit is an elastic member, the elastic member comprises a first electrode and a second electrode, the first electrode and the second electrode form a capacitive sensing device.

6. The intraocular pressure detecting device of claim 5, wherein the elastic member further comprises a third electrode, the third electrode is disposed between the first electrode and the second electrode to raise the signal-to-noise ratio.

7. The intraocular pressure detecting device of claim 6, wherein the elastic member further comprises a reference electrode, the reference electrode directly detects vibrations of the intraocular pressure detection area.

8. An intraocular pressure detecting device, comprising:
an image capturing unit for capturing an eye image;
a processor unit electrically coupled to the image capturing unit for determining an intraocular pressure detection area according to the eye image;
a pressure detection unit for detecting the intraocular pressure detection area and generating a pressure detection signal, wherein the processor unit determines an intraocular pressure according to the pressure detection signal, and wherein the pressure detection unit is an elastic member, the elastic member comprises a first electrode and a second electrode, the first electrode and the second electrode form a capacitive sensing device.

9. The intraocular pressure detecting device of claim 8, wherein the image capturing unit comprises a photographic device, the photographic device capturing the eye image.

10. The intraocular pressure detecting device of claim 9, wherein the eye image is selected from a cornea image, an eyelid image, an eyebrow image, and an orbit image.

11. The intraocular pressure detecting device of claim 10, wherein the eye image comprises corneal thickness data, corneal section image data, and corneal curvature data.

12. The intraocular pressure detecting device of claim 8, wherein the processor unit comprises an analog-to-digital converter and a microprocessor, the analog-to-digital converter processes the eye image into an eye image signal, the micro-processor analyzes the eye image signal and determines the intraocular pressure detection area.

13. The intraocular pressure detecting device of claim 8, wherein the elastic member further comprises a third electrode, the third electrode is disposed between the first electrode and the second electrode to raise the signal-to-noise ratio.

14. The intraocular pressure detecting device of claim 13, wherein the elastic member further comprises a reference electrode, the reference electrode directly detects vibrations of the intraocular pressure detection area.

* * * * *